US010466381B2

(12) United States Patent
Coman

(10) Patent No.: US 10,466,381 B2
(45) Date of Patent: Nov. 5, 2019

(54) NMR LOGGING IN FORMATION WITH MICRO-POROSITY BY USING FIRST ECHOES FROM MULTIPLE MEASUREMENTS

(71) Applicant: Radu Coman, Hannover (DE)

(72) Inventor: Radu Coman, Hannover (DE)

(73) Assignee: BAKER HUGHES, A GE COMPANY, LLC, Houston, TX (US)

( * ) Notice: Subject to any disclaimer, the term of this patent is extended or adjusted under 35 U.S.C. 154(b) by 528 days.

(21) Appl. No.: 14/979,998

(22) Filed: Dec. 28, 2015

(65) Prior Publication Data

US 2017/0184755 A1 Jun. 29, 2017

(51) Int. Cl.
*G01V 3/32* (2006.01)
*G01R 33/44* (2006.01)
*G01N 15/08* (2006.01)

(52) U.S. Cl.
CPC .............. *G01V 3/32* (2013.01); *G01R 33/448* (2013.01); *G01N 15/088* (2013.01)

(58) Field of Classification Search
None
See application file for complete search history.

(56) References Cited

U.S. PATENT DOCUMENTS

| 4,318,043 | A |   | 3/1982  | Crooks et al. |
| 5,023,551 | A |   | 6/1991  | Kleinberg et al. |
| 5,486,762 | A | * | 1/1996  | Freedman ............ G01N 24/081 324/303 |
| 5,798,643 | A |   | 8/1998  | Werthner |
| 6,051,973 | A |   | 4/2000  | Prammer |
| 6,069,477 | A | * | 5/2000  | Chen .................... G01N 24/081 324/303 |
| 6,121,774 | A |   | 9/2000  | Sun et al. |
| 6,163,153 | A |   | 12/2000 | Reiderman et al. |
| 6,215,304 | B1 |  | 4/2001  | Slade |
| 6,331,775 | B1 |  | 12/2001 | Thern et al. |

(Continued)

OTHER PUBLICATIONS

Coman et al. "Improved NMR Logging Approach to Simultaneously Determine Porosity, T2 and T1", SPE (Society of Petroleum Engineers), Sep. 2015, pp. 1-27.*
PetroWiki, "Porosity determination with NMR logging" Society of Petroleum Engineers (SPE international), pp. 1-7, Jun. 24, 2015.*
Xie et al. "Advanced fluid-typing methods for NMR", Jan. 14, 2010, Pet Sci (2011), pp. 163-169. (Year: 2010).*

(Continued)

*Primary Examiner* — Telly D Green
(74) *Attorney, Agent, or Firm* — Cantor Colburn LLP

(57) ABSTRACT

A method for estimating a property of a subsurface material includes: conveying a carrier through a borehole penetrating the subsurface material; performing at least two magnetic resonance (NMR) measurements in a volume of interest in the subsurface material using an NMR tool disposed on the carrier, wherein (i) a first NMR measurement has a first wait time and a first first-echo time and a second NMR measurement has a second wait time and a second first-echo time, (ii) the first wait time and the second wait time are less than or equal to 500 milliseconds, and (iii) the first first-echo time and the second first-echo time are different; receiving at least the first-echo of the first NMR measurement and receiving at least the first-echo of the second NMR measurement; and estimating the property of the subsurface material by using the at least two measured first-echoes simultaneously.

23 Claims, 5 Drawing Sheets

(56) References Cited

U.S. PATENT DOCUMENTS

| | | | |
|---|---|---|---|
| 6,392,409 B1* | 5/2002 | Chen | G01N 24/081 324/303 |
| 6,498,484 B1* | 12/2002 | Sun | G01N 24/081 324/303 |
| 6,600,315 B1 | 7/2003 | Heaton et al. | |
| 6,891,369 B2 | 5/2005 | Hurlimann et al. | |
| 7,301,337 B2 | 11/2007 | Beard | |
| 7,528,600 B2 | 5/2009 | Sen et al. | |
| 2003/0016013 A1 | 1/2003 | Kruspe et al. | |
| 2003/0071620 A1 | 4/2003 | Reiderman et al. | |
| 2003/0085702 A1 | 5/2003 | Freed et al. | |
| 2003/0132749 A1 | 7/2003 | Speier et al. | |
| 2004/0008027 A1* | 1/2004 | Prammer | G01N 24/081 324/303 |
| 2004/0257075 A1* | 12/2004 | An | G01N 24/081 324/303 |
| 2005/0104587 A1* | 5/2005 | Akkurt | G01N 24/081 324/303 |
| 2008/0024128 A1 | 1/2008 | Song et al. | |
| 2010/0023786 A1* | 1/2010 | Liberman | H02J 3/14 713/320 |
| 2010/0237865 A1* | 9/2010 | Stemmer | G01R 33/5611 324/309 |
| 2010/0283460 A1 | 11/2010 | Kruspe et al. | |
| 2013/0200890 A1* | 8/2013 | Hursan | G01V 3/32 324/303 |
| 2015/0022202 A1 | 1/2015 | Song et al. | |
| 2015/0241541 A1* | 8/2015 | Blanz | G01R 33/56509 324/303 |
| 2016/0047936 A1* | 2/2016 | Ali | G01V 3/32 324/303 |
| 2016/0116629 A1* | 4/2016 | Coman | G01V 3/32 324/303 |
| 2016/0320519 A1* | 11/2016 | Blanz | G01V 3/32 |
| 2016/0334533 A1* | 11/2016 | Coman | G01V 3/32 |

OTHER PUBLICATIONS

Moritz "NMR tools afford new logging choices", Apr. 17, 2000, Oil & Gas Journal, pp. 1-16. (Year: 2000).*

Schlumberger et al. "How to Use Borehole Nuclear Magnetic Resonance", Oilfield Review, pp. 34-57. (Year: 1997).*

Freedmen "Advances in NMR Logging", Jan. 2006, JPT, pp. 60-66 (Year: 2006).*

Akkurt, et al. "Enhanced Diffusion Expanding The Range of NMR Direct HydroCarbon-Typing Applications"; SPWLA 39th Annual Logging Symposium, May 26-29, 1998; 14 pages.

Coates, et al.; "NMR Logging Principles & Applications"; Halliburton Energy Services; (1999); Part one; 131 pages.

Coates, et al.; "NMR Logging Principles & Applications"; Halliburton Energy Services; (1999); Part Two; 116 pages.

Dodge, et al.; "A Case Study Demonstrating How NMR Logging Reduces Completion Uncertainties in Low Porosity, Tight Gas Sand Reservoirs"; SPWLA 39th Annual Logging Symposium, May 26-29, 1998; 14 pages.

Dunn, et al.; "NMR Relaxation";Nuclear Magnetic Resonance Petrophysical and Logging Applications; PERGAMON (2002). 10 pages.

Goelman, et al.; "The CPMG Pulse Sequence in Strong Magnetic Field Gradients with Applications to Oil-Well Logging"; Journal of Magnetic Resonance Series A 113, 11-18 (1995); 8 pages.

International Search Report and the Written Opinion of the International Searching Authority, or the Declaration; PCT/US2016/031819; dated Sep. 13, 2016; 7 pages.

Prammer, et al.; "Measurements of Clay-Boound Water and Total Porosity by Magnetic Resonance Logging"; SPE 36522; (1996); 10 pages.

International Search Report and the Written Opinion of the International Searching Authority, or the Declaration; PCT/US2016/064680; dated Mar. 20, 2017; 14 pages.

* cited by examiner

NMR LOGGING IN FORMATION WITH MICRO-POROSITY BY USING FIRST ECHOES FROM MULTIPLE MEASUREMENTS

BACKGROUND

Boreholes are drilled into the earth for many applications such as hydrocarbon production, geothermal production, and carbon dioxide sequestration. In order to efficiently use expensive resources drilling the boreholes, it is important for analysts to acquire detailed information related to the geologic formations being drilled.

Nuclear magnetic resonance (NMR) tools are one type of downhole tools that are particularly useful for performing detailed measurements of properties of hydrocarbon bearing formations or overburden shale. NMR measurements are used to determine among other things, porosity, hydrocarbon saturation, and permeability of rock formations. In overburden shale, the porosity may be due to clay-bound water since there may be is no hydrocarbon in this shale. The NMR logging tools are used to excite the atomic nuclei of the fluids in the geological formations surrounding the borehole so that certain NMR parameters such as NMR porosity, longitudinal relaxation time (generally referred to in the art as $T_1$) and transverse relaxation time (generally referred to in the art as $T_2$) of the geological formations can be measured. From such measurements, the porosity, permeability and hydrocarbon saturation are determined, which provide valuable information about the make-up of the geological formations and the amount of extractable hydrocarbons. The following references may be referred to for teachings with respect to performing NMR measurements: NMR LOGGING PRINCIPLES & APPLICATIONS by George R. Coates, Lizhi Xiao, and Manfred G. Prammer, Halliburton Energy Services Publication H02308 (1999); Nuclear Magnetic Resonance Petrophysical and Logging Applications by K.-J. DUNN, D. J. Bergman and G. A. Latorraca, PERGAMON (2002); and U.S. Pat. No. 6,051,973 to Manfred Prammer.

Determining in particular fast decaying partial porosities at downhole conditions has been challenging. Prammer et al. (Prammer et al., SPE Annual Technical Conference and Exhibition, Denver 6-9 Oct. 1996, SPE-36522) describes a method to separately determine fast decaying partial porosities by performing two NMR measurements with a short and a long wait time. Prammer et al. records two echo trains and estimates a fast and slowly decaying porosity. Akkurt et al. (Akkurt et al. SPWLA 39th Annual Logging Symposium, Keystone, Colo., 26-28 May 1998, SPWLA-GG) describes a so-called "dual-TE method" to determine the fluid diffusion coefficient by utilizing two NMR measurements with equal wait time and different inter-echo times. The wait time for the two NMR measurements is long in order to polarize all of the formation fluid. The fluid diffusion coefficient is estimated from the two echo trains that are recorded with the two NMR measurements.

Unfortunately, an NMR effect, here referred to as the second-order stimulated-echo effect, disturbs the amplitude of indirect NMR echoes. The theoretical background for this effect was presented by Goelman and Prammer (Goelman, G. and Prammer, M. G. 1995, The CPMG Pulse Sequence in Strong Magnetic Field Gradients with Applications to Oil-Well Logging, Journal of Magnetic Resonance, Series A 113: 11-18). However Goelman and Prammer do not mention the consequence of the second-order stimulated echo effect on the porosity in geological formations with micro-porosity. The disturbance leads to distortion of an NMR signal and is significant in formations with NMR micro-porosity (e.g., shale gas, shale oil, clay-bound water, heavy oil, tar, carbonates). Due to the second-order stimulated-echo effect prior art NMR logging methods can lead to inaccurate estimates of micro-porosities where the estimates can be inaccurate by 20% or even more. Hence, it would be well received in the drilling and production industries, if methods and systems could be developed to reduce or eliminate the distortion of the NMR signal due to the second-order stimulated-echo effect.

BRIEF SUMMARY

Disclosed is a method for estimating a property of a subsurface material. The method includes: conveying a carrier through a borehole penetrating the subsurface material; performing at least two magnetic resonance (NMR) measurements in a volume of interest in the subsurface material using an NMR tool disposed on the carrier, wherein (i) a first NMR measurement has a first wait time and a first first-echo time and a second NMR measurement has a second wait time and a second first-echo time, (ii) the first wait time and the second wait time are less than or equal to 500 milliseconds, and (iii) the first first-echo time and the second first-echo time are different; receiving, by a processor, at least the first-echo of the first NMR measurement and receiving at least the first-echo of the second NMR measurement; and estimating, by the processor, the property of the subsurface material by using the at least two measured first-echoes simultaneously.

Also disclosed is an apparatus for estimating a property of a subsurface material. The apparatus includes a carrier configured to be conveyed through a borehole penetrating the subsurface material, a nuclear magnetic resonance (NMR) tool disposed on the carrier and a processor. The NMR tool is configured to perform at least two magnetic resonance (NMR) measurements in a volume of interest in the subsurface material using an NMR tool disposed on the carrier, wherein (i) a first NMR measurement has a first wait time and a first first-echo time and a second NMR measurement has a second wait time and a second first-echo time, (ii) the first wait time and the second wait time are less than or equal to 500 milliseconds, and (iii) the first first-echo time and the second first-echo time are different. The processor is configured to: receive at least the first-echo of the first NMR measurement and receive at least the first-echo of the second NMR measurement; and estimate the property of the subsurface material by using the at least two measured first-echoes simultaneously.

BRIEF DESCRIPTION OF THE DRAWINGS

The following descriptions should not be considered limiting in any way. With reference to the accompanying drawings, like elements are numbered alike.

DETAILED DESCRIPTION

Figure 1:
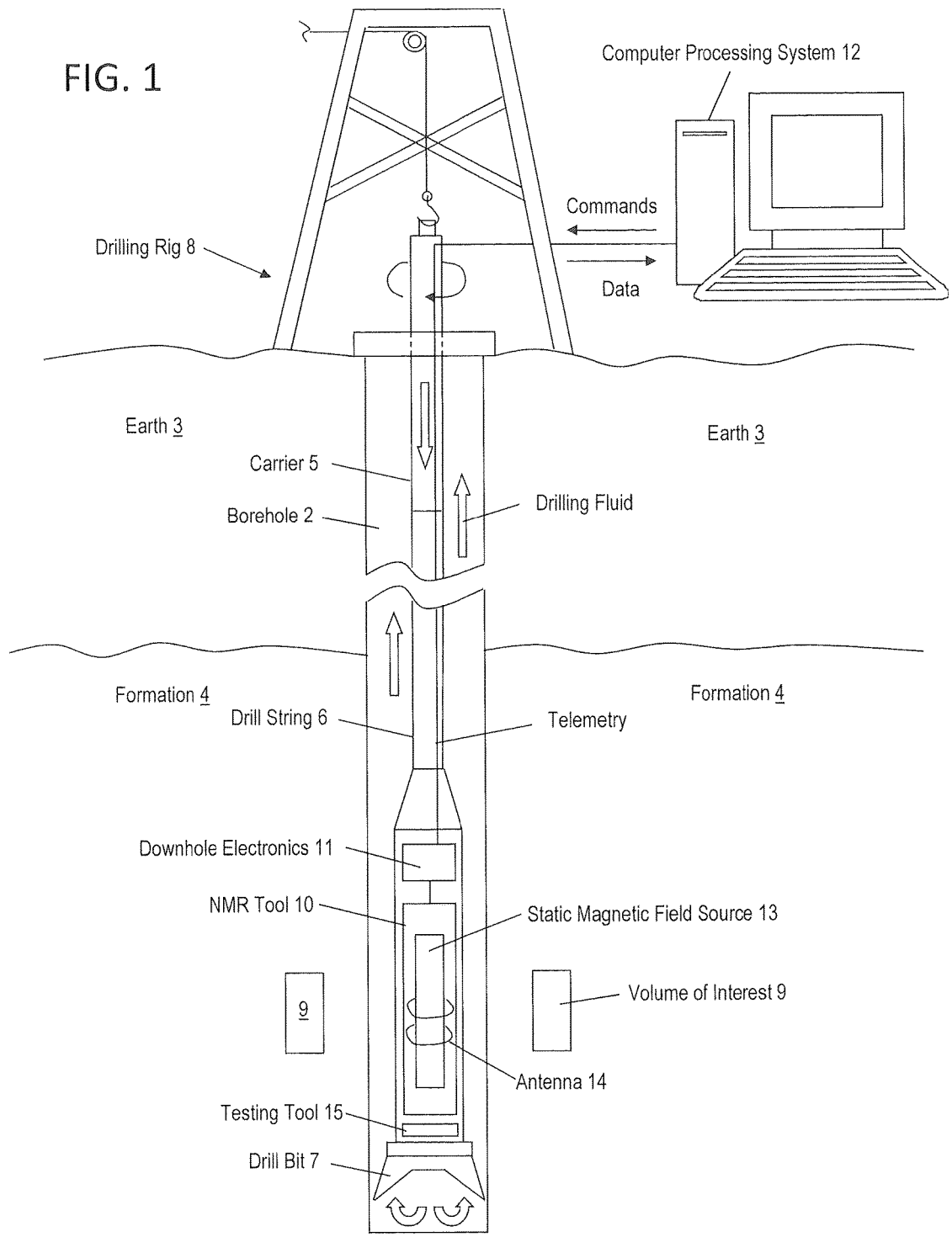
FIG. 1 illustrates a cross-sectional view of an embodiment of a downhole nuclear magnetic resonance (NMR) tool disposed in a borehole penetrating the earth.

A detailed description of one or more embodiments of the disclosed apparatus and method presented herein by way of exemplification and not limitation with reference to the figures.

Disclosed are method and system a new nuclear magnetic resonance (NMR) logging method that reduces or eliminates the distortion of an NMR signal due to the second-order stimulated-echo effect. The second-order stimulated-echo effect is caused by the inhomogeneity of the static magnetic field, $B_0$, and this effect may occur for all NMR logging tools (both LWD and wireline). The method includes NMR echo acquisition by using at least two NMR measurements with very short wait times (e.g., less than 100 milliseconds (ms) and with different first-echo times (e.g., 0.4 ms and 0.5 ms), and the simultaneous processing of the first-echoes to obtain a property of interest (e.g., porosity, $T_2$). For convenience, the method disclosed herein may be referred to as the "dual first-echo method". However, the method is not restricted to two NMR measurements and the additional acquisition and processing of echoes is part of the current disclosure.

As disclosed herein, one implementation of the method includes: (1) the acquisition of a first first-echo by a first NMR measurement having a very short wait time (e.g., less than 100 ms) and a given first-echo time (e.g., 0.4 ms); (2) the acquisition of a second first-echo by a second measurement having the same wait time as the first measurement but a different first-echo time (e.g., 0.5 ms); and (3) the simultaneous processing of the two first-echoes from the two measurements to evaluate a property of interest (e.g., porosity, $T_2$). The disclosure is not limited to the second measurement having the same wait time. It might have a differing wait time.

NMR micro-porosity ("short-$T_2$ porosity" where $T_2$ is less than or equal to 6 ms) provides useful information both for conventional as well as for unconventional reservoirs. In an unconventional reservoir, the NMR micro-porosity is directly linked to the potential reserves (e.g., shale gas, shale oil). In a reservoir with heavy oil or with tar, the NMR micro-porosity is the porosity of these hydrocarbon components. In a conventional reservoir, the NMR micro-porosity is the porosity of the clay-bound water and this porosity is important for the estimation of irreducible water saturation, the estimation of the permeability and the computation of several other NMR answer products (e.g., hydrocarbon saturation). In a carbonate reservoir, the NMR micro-porosity is directly related to the petrophysical micro-porosity. The micro-porosity in carbonates is a parameter used for formation evaluation in carbonates (e.g., total porosity, permeability, saturation). In the overburden, the NMR micro-porosity is the porosity of the shale. Knowing the porosity of the shale and/or the associated $T_2$ value (which is usually computed as the geometric mean of the $T_2$ distribution of the micro-porosity peak) also provides useful information because it might be an indicator for pore (over) pressure and it might be an indicator for shale mineralogy, which is useful for wellbore stability and casing decisions.

Next, apparatus for implementing the method and system disclosed herein is discussed. FIG. 1 illustrates a cross-sectional view of an embodiment of an NMR tool 10 disposed in a borehole 2 penetrating the earth 3, which includes an earth formation 4. The NMR tool 10 is conveyed through the borehole 2 by a carrier 5, which can be a drill tubular such as a drill string 6. A drill bit 7 is disposed at the distal end of the drill string 6. A drill rig 8 is configured to conduct drilling operations such as rotating the drill string 6 and thus the drill bit 7 in order to drill the borehole 2. In addition, the drill rig 8 is configured to pump drilling mud (i.e., drill fluid) through the drill string 6 in order to lubricate the drill bit 7 and flush cuttings from the borehole 2. Downhole electronics 11 are configured to operate the NMR tool 10, process measurement data obtained downhole, and/or act as an interface with telemetry to communicate data or commands between downhole components and a computer processing system 12 disposed at the surface of the earth 3. Non-limiting embodiments of the telemetry include pulsed-mud, wired drill pipe, fiberoptics, electromagnetic, acoustic and any other possible transmission method for real time communications. System operation and data processing operations may be performed by the downhole electronics 11, the computer processing system 12, or a combination thereof. In an alternative embodiment, the carrier 5 may be an armored wireline, which can support and convey the NMR tool 10 and also provide a conductor for communications with the surface processing system 12.

The NMR tool 10 is configured to perform NMR measurements on the formation 4. NMR measurements are performed in a volume of interest 9. This volume may be torus-shaped, surrounding the NMR tool 10, or, when using a side-looking NMR tool, may be on one side only. The NMR measurements may yield a longitudinal relaxation time constant $T_1$ and a transverse relaxation time constant $T_2$ (or distributions thereof, see below). $T_1$ relates to a time that is characteristic of the amount of time required for magnetic polarization of the hydrogen atoms in the volume of interest. In general, longer wait times (TW) provide more magnetic polarization than shorter wait times. $T_2$ relates to an exponential decay time constant that corresponds to a characteristic or property of the formation 4 material. Transverse relaxation relates to the irreversible loss of phase coherence of individual hydrogen nuclei (=protons) in the formation 4 material while precessing about a static magnetic field during an NMR measurement. There is not one single value of $T_2$ for formation rock but a wide distribution of values lying anywhere between fractions of a millisecond (ms) and several seconds for example. The distributions of $T_1$ and $T_2$ values are principal outputs of the NMR tool 10 and together may be referred to as an NMR partial porosity log. Components in the NMR tool 10 include a static magnetic field source 13 that magnetizes formation materials and an antenna 14, which may represent one or more antennas, which transmit precisely timed bursts of radio-frequency energy (e.g., a CPMG sequence) that provides an oscillating magnetic field. In a time period between these pulses, the antenna receives a decaying echo signal from those protons that have been excited. Because a linear relationship exists between the proton resonance frequency and the strength of the static magnetic field, the frequency of transmitted radio-frequency energy can be tuned to investigate volumes of interest having different diameters around the NMR tool 10. It can be appreciated that the NMR tool 10 may include a variety of components and configurations as known in the art of NMR. In that NMR tools are known in the art, specific details of components and configurations of these tools are not discussed in further detail.

It can be appreciated that the NMR tool 10 may be calibrated to a known micro-porosity and/or other known properties of a subsurface material by analysis or by testing in field or laboratory conditions using subsurface materials having a known micro-porosity and/or other known properties.

A testing tool 15 may also be disposed on the carrier 5. The testing tool 15 is configured to extract a sample of formation fluid through a wall of the borehole 2 at a determined point and test the sample to estimate a property of the sampled fluid. Alternatively or in addition to the testing, the sample may be stored for analysis at the surface. Sampling points may be determined based upon output received from the NMR tool 10.

It can also be appreciated that the drill rig 8 may also be configured to perform completion actions for completing the borehole 2. For example, the drill rig 8 may be used to lower a perforating gun using the carrier 5 in order to perforate a casing lining the borehole 2 at specific locations based upon data received from the NMR tool 10. Production actions may also be performed by the drill rig 8 based upon data received from the NMR tool 10. For example, a hydrocarbon pumping rate implemented by the drill rig 8 may be determined using data received from the NMR tool 10.

Next, processing of NMR signals is discussed. NMR logging data acquisition is generally performed with a Carr-Purcell-Meiboom-Gill (CPMG) pulse sequence as known in the art. The first echo of a CPMG pulse sequence is a direct echo while all other echoes are a sum of a direct echo and one or more indirect echoes (see e.g., Goelman, G. and Prammer, M. G. 1995, The CPMG Pulse Sequence in Strong Magnetic Field Gradients with Applications to Oil-Well Logging, Journal of Magnetic Resonance, Series A 113: 11-18.). Thus, all CPMG echoes except the first echo are composite echoes.

A direct echo is a pure spin echo decaying with a particular relaxation time, $T_{2A}$, i.e., the spins which form a direct echo relaxes only in the x-y plane (transversal plane). $T_{2A}$ is the apparent $T_2$ and can be expressed as:

$$\frac{1}{T_{2A}} = \frac{1}{T_{2I}} + \frac{1}{T_{2D}},$$

where $T_{2I}$ is the intrinsic $T_2$ relaxation time and $T_{2D}$ is the $T_2$ relaxation time caused by diffusion in the magnetic field gradient. $T_{2D}$ depends on the inter-echo time, TE, on the molecular diffusion coefficient, D, and on the internal field gradient, G. $T_{2I}$ can be expressed as:

$$\frac{1}{T_{2I}} = \frac{1}{T_{2B}} + \frac{1}{T_{2S}},$$

where $T_{2B}$ is the $T_2$ relaxation time of the bulk fluid and is inverse proportional to the viscosity, i.e., $T_{2B}$ of very heavy oil is very short. $T_{2S}$ is caused by surface relaxation and is proportional to the pore size, i.e., $T_{2S}$ is very short in shale (shale gas, shale oil, clay-bound water).

An indirect echo is an echo whose coherence pathway crosses the z-direction (longitudinal direction). The most significant indirect echo is the stimulated echo. An indirect echo is not decaying continuously in the transversal plane (with the decay rate $T_{2A}$). For a period of time between two pulses an indirect echo is decaying in the longitudinal direction with a $T_{1A}$ relaxation time. $T_{1A}$ is the apparent $T_1$ (or "effective" $T_1$) and can be expressed as (see Prammer et al. 1995):

$$\frac{1}{T_{1A}} = \frac{1}{T_{1I}} + \frac{1}{T_{1D}},$$

where $T_{1I}$ is the intrinsic $T_1$ relaxation time and $T_{1D}$ is the $T_1$ relaxation time caused by diffusion in the magnetic field gradient. $T_{1D}$ depends on the inter-echo time, TE, on the molecular diffusion coefficient, D, and on the internal field gradient, G. $T_{1I}$ can be expressed as:

$$\frac{1}{T_{1I}} = \frac{1}{T_{1B}} + \frac{1}{T_{1S}},$$

where $T_{1B}$ is the $T_1$ relaxation time of the bulk fluid, and $T_{2S}$ is caused by surface relaxation. Note that $T_{1A}$ refers only to the echo decay process. The longitudinal magnetization is controlled only by $T_{1I}$ (Prammer et al. 1995). In general, $T_{1I} > T_{2I}$ and $T_{1D} < T_{2D}$. Therefore, there is no general rule whether $T_{1A} > T_{2A}$ or $T_{1A} < T_{2A}$. In the absence of relaxation ($T_{1A} = T_{2A} = $ infinite), numerical simulation shows that the composite echoes tend to a constant value and this value is already reached at the 4th echo.

The deviating amplitude of the first few echoes is known as the stimulated-echo effect and will be referred to herein as the "first-order stimulated-echo effect". Adjusting the amplitudes of these echoes to the amplitude of the rest of the echoes is known as the "stimulated-echo correction" (see e.g., Coates, G. R., Xiao, L., and Prammer, M. G. 1999. NMR logging: principles and applications. Houston: Halliburton Energy Services, page 194) or the "first-order stimulated-echo correction".

The first-order stimulated-echo correction is sufficient, if the relaxation of the indirect echoes in the x-y plane is similar to the relaxation of the echoes in the z-direction ($T_{1A}$ is approximately $T_{2A}$). Theoretical insights and laboratory experiments indicate that the correction is sufficient as long as $T_{2A}$ is significantly larger than the inter-echo time (e.g., $T_{2A} > 10$ ms).

If $T_{2A}$ is comparable with the inter-echo time, then the relaxation of the indirect echo in the z-direction (with a different relaxation rate than in the x-y plane) will change the amplitude of the indirect echo significantly (with respect to the reference case which assumes $T_{1A} = T_{2A}$). As a consequence the amplitude of all composite echoes will change. This is what is called in this disclosure as the "second-order stimulated-echo effect".

The second-order stimulated-echo effect causes inaccurate porosities and $T_2$ relaxation times in formations with NMR micro-porosity (i.e., short-$T_2$ values such as less than or equal to 6 ms for example).

Next, the method disclosed herein (referred to herein as the dual first-echo method) is discussed in detail. The implementation of the NMR logging method disclosed herein includes the following steps: (1) NMR acquisition; (2) NMR data processing in time domain; (3) NMR data transformation from time domain into the $T_2$ domain; and (4) NMR data processing in the $T_2$ domain to obtain a property of interest. Each of these steps is discussed in detail below.

Next, the NMR acquisition step is discussed. The NMR acquisition or activation includes two measurements having very short wait times (e.g., less than 100 ms) and different first-echo times (e.g., 0.4 ms and 0.5 ms). A measurement with a very short wait time is referred to as a micro-porosity measurement. Usually a micro-porosity measurement is a CPMG pulse sequence measurement (a so-called trainlet). The CPMG trainlet is one example of implementation. However, a CPMG pulse sequence is not required. A pulse sequence with only two pulses (a so-called Hahn pulse sequence) is sufficient.

In general, the wait times of the two micro-porosity measurements are selected to be the same. However, this disclosure also covers the case where the wait times are different (but both of them are less or equal to 500 ms).

To reduce the effect of ringing on the first echo, the acquisition with frequency dithering is recommended (Beard D. 2003. Frequency dithering to avoid excitation pulse ringing. U.S. Pat. No. 7,301,337.).

In some cases the acquisition of only two micro-porosity measurements is not sufficient. Additional measurements which can be used are: a third micro-porosity measurement having the same wait time as the other two, but a different first-echo time (e.g., 0.6 ms); a measurement with a long wait time, a so-called total-porosity measurement (the "long wait time" is generally between 6 seconds and 16 seconds); a measurement with a short wait time, a so-called partial-porosity measurement (the "short wait time" is generally between 1 second and 3 seconds); and other measurements which are known in the art of NMR logging (e.g., dual wait time, dual inter-echo time, see e.g., Coates, G. R., Xiao, L., and Prammer, M. G. 1999. NMR logging: principles and applications. Houston: Halliburton Energy Services). Usually, the total-porosity measurement and the partial-porosity measurement are CPMG pulse sequences recorded in a phase-alternate-pair (PAP) procedure. Also usually, the NMR echoes are recorded in two orthogonal channels (the x-channel and the y-channel).

Next, the NMR data processing in a time domain step is discussed. The NMR data processing in time domain may include one or more of the following.
(1) Combining multiple measurements recorded in a frequency-dithering mode or in a phase-alternate-pair mode into a single measurement; echo de-spiking, which removes/replaces/corrects spiky i.e., unexpected high or low amplitude echoes.
(2) Calibration, which scales the amplitude of the echoes to reflect the porosity in the sensed formation. The calibration is a function of the type of acquisition used. For a CPMG acquisition, there is a calibration value which applies to all echoes and the first-order stimulated-echo correction which applies only to the first few echoes (typically the first three echoes).
(3) Phase rotation, which rotates the x-channel and the y-channel data into a "signal channel" and a "noise channel."
(4) Averaging, which averages consecutive measurements in a "running average" fashion to improve the signal-to-noise ratio.
(5) Environmental correction (e.g., temperature, axial motion, lateral motion).

Next, the NMR data transformation from time domain into the $T_2$ domain step is discussed. This action is related to the "NMR acquisition." Several examples follow. For these examples it is assumed that (1) for the first micro-porosity measurement: the time of the first echo is $\tau_A$ and the amplitude of the first echo is $E_{1A}$ and (2) for the second micro-porosity measurement: the time of the first echo is $\tau_B$ and the amplitude of the first echo is $E_{1B}$.

For the first example, if the NMR acquisition includes only two micro-porosity measurements and the formation has only a single micro-porosity peak then the amplitudes of the first-echo read for the two measurements are:

$$E_{1A} = \emptyset_\mu \cdot e^{-\frac{\tau_A}{T_{2\mu}}} \quad (1)$$

$$E_{1B} = \emptyset_\mu \cdot e^{-\frac{\tau_B}{T_{2\mu}}} \quad (2)$$

where $T_{2\mu}$ is the geometric mean $T_2$ value and $\emptyset_\mu$ is the NMR micro-porosity. Equations (1) and (2) form a system with two equations and two unknowns which can be directly solved for the two unknowns ($T_{2\mu}$ and $\emptyset_\mu$).

In the second example, even if the formation is known to have only a single micro-porosity peak, it is recommended to use an activation with three micro-porosity measurements. In this case, the amplitudes of the first-echo can be expressed as:

$$E_{1A} = \emptyset_\mu \cdot e^{-\frac{\tau_A}{T_{2\mu}}} + E_r \quad (3)$$

$$E_{1B} = \emptyset_\mu \cdot e^{-\frac{\tau_B}{T_{2\mu}}} + E_r \quad (4)$$

$$E_{1C} = \emptyset_\mu \cdot e^{-\frac{\tau_C}{T_{2\mu}}} + E_r \quad (5)$$

where $E_r$ is assumed to be a constant term. Equations 3-5 build a system of three equations with three unknowns which can be solved mathematically.

In a third example, if the NMR acquisition includes two micro-porosity measurements and a total-porosity measurement, then the amplitudes of the first-echo of the micro-porosity measurement can be expressed as:

$$E_{1A} = \emptyset_\mu \cdot e^{-\frac{\tau_A}{T_{2\mu}}} + \sum_{i=1}^{n} \emptyset_i \cdot e^{-\frac{\tau_A}{T_{2,i}}} \quad (6)$$

$$E_{1B} = \emptyset_\mu \cdot e^{-\frac{\tau_B}{T_{2\mu}}} + \sum_{i=1}^{n} \emptyset_i \cdot e^{-\frac{\tau_B}{T_{2,i}}} \quad (7)$$

where i is the number of the porosity bin except the NMR micro-porosity bin and n is the number of bins. Within an NMR activation, the micro-porosity measurement is generally repeated more times than the total-porosity measurement. This improves the signal-to-noise ratio of the echoes in the micro-porosity measurement. The effect of the non-micro-porosity ("sum-term") on the amplitude of the recorded echoes in Eq. 6 and Eq. 7 can be estimated from the inverted $T_2$ distribution from the total-porosity measurement. Alternatively other inversion methods known in the NMR logging prior art might be used. Two useful inversion methods are: (1) the "separate inversion" method where the data from the micro-porosity acquisition and data from the echo train are inverted separately and the results are merged after inversion and (2) the "joint inversion" method where the data from the micro-porosity acquisition and data from the echo train are inverted simultaneously.

In the fourth example, three micro-porosity measurements and a total-porosity measurement are obtained. Multiple inversion schemes are possible.

In the fifth example, three micro-porosity measurements, a total-porosity measurement, and a partial-porosity measurement are obtained. Multiple inversion schemes are possible.

Next, the NMR data processing in the $T_2$ domain to obtain a property of interest step is discussed. This step includes prior art NMR processing methods to obtain NMR answer products such as partial porosities, permeabilities, saturations, viscosity, hydrogen index, pore size, grain size, wettability, producibility, and/or diffusion.

Next, numerical simulations are discussed. In this section, the standard NMR logging method based on a single CPMG trainlets compared with the new dual first-echo method as disclosed herein. The comparison is based on a simple numerical simulation and a single exponential fit. The input data for the simulation are: NMR micro-porosity: 10 p.u.; Geometric mean $T_2$: 0.4 ms; Noise on echoes: 0 p.u.; Inter-echo time of first trainlet: 0.4 ms; and Inter-echo time of second trainlet: 0.5 ms.

Figure 2:
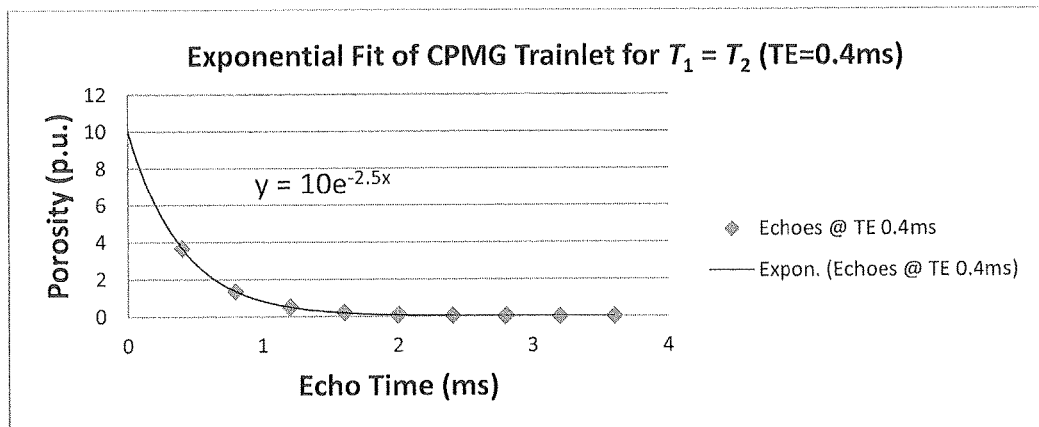
FIG. 2 depicts aspects of an exponential fit of a CPMG trainlet with an inter-echo time of 0.4 ms for the case of $T_1 = T_2$.
Figure 3:
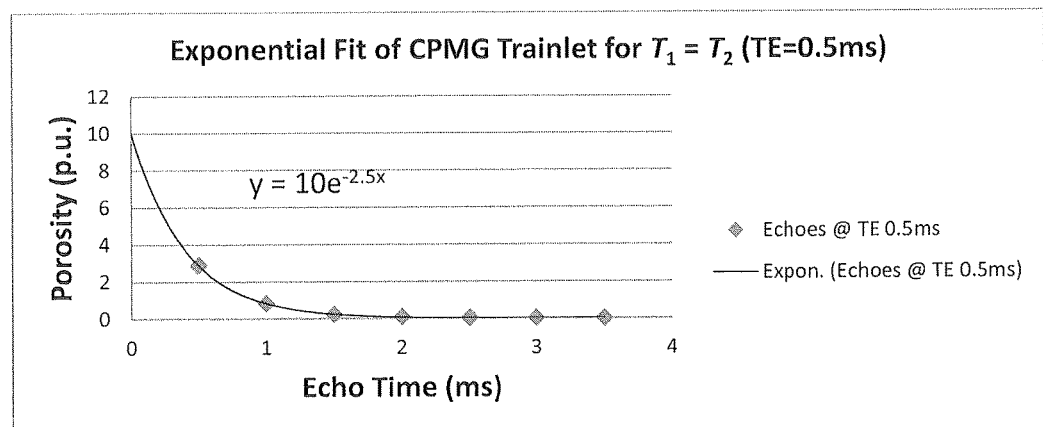
FIG. 3 depicts aspects of an exponential fit of a CPMG trainlet with an inter-echo time of 0.5 ms for the case $T_1 = T_2$.
Figure 4:
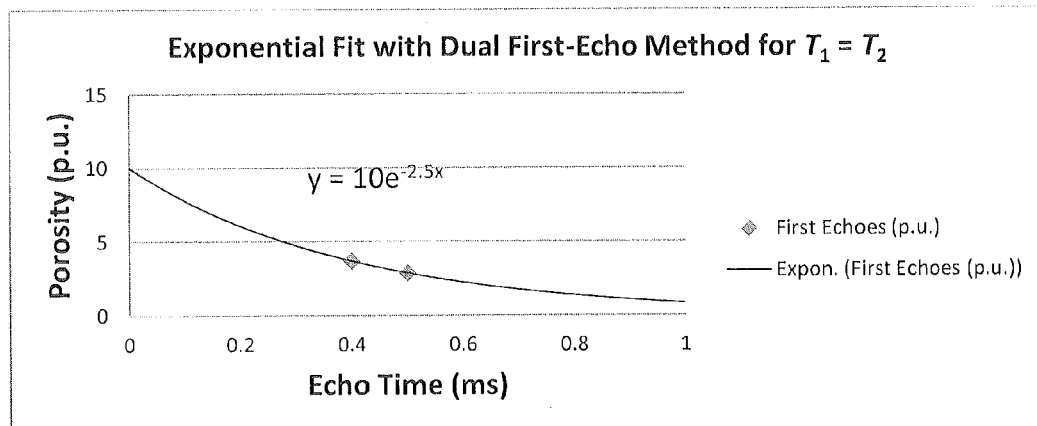
FIG. 4 depicts aspects of an exponential fit with a dual-first echo method for the case $T_1 = T_2$.

In a first simulation case, $T_1$ equals $T_2$. FIG. 2 illustrates an exponential fit of a CPMG trainlet with an inter-echo time of 0.4 ms for the case $T_1=T_2$. The estimated porosity is 10 p.u. (porosity units) and the estimated $T_2$ is 0.4 ms. FIG. 3 illustrates an exponential fit of a CPMG trainlet with an inter-echo time of 0.5 ms for the case $T_1=T_2$. The estimated porosity is 10 p.u. and the estimated $T_2$ is 0.4 ms. FIG. 4 illustrates an exponential fit with the dual fist-echo method for the case $T_1=T_2$. The first echoes are recorded at the time of 0.4 ms and 0.5 ms. The estimated porosity is 10 p.u. and the estimated $T_2$ is 0.4 ms. If $T_1=T_2$ then both the standard acquisition and processing method as well as the new dual first-echo methods delivers an accurate porosity and $T_2$ value.

Figure 5:
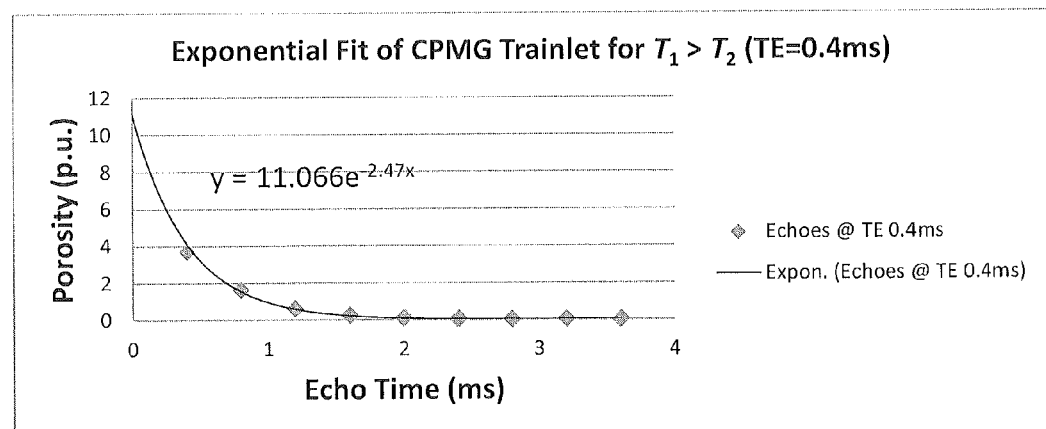
FIG. 5 depicts aspects of an exponential fit of a CPMG trainlet with an inter-echo time of 0.4 ms for the case $T_1 > T_2$.
Figure 6:
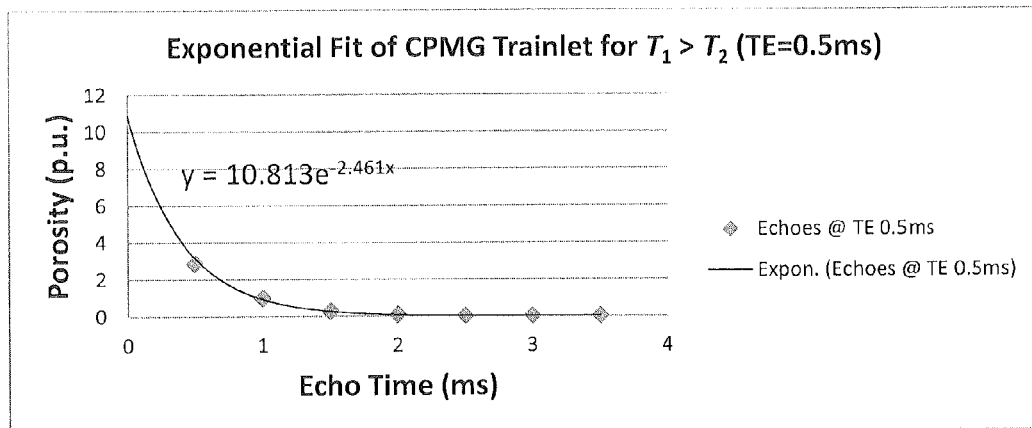
FIG. 6 depicts aspects of an exponential fit of a CPMG trainlet with an inter-echo time of 0.5 ms for the case $T_1 > T_2$.
Figure 7:
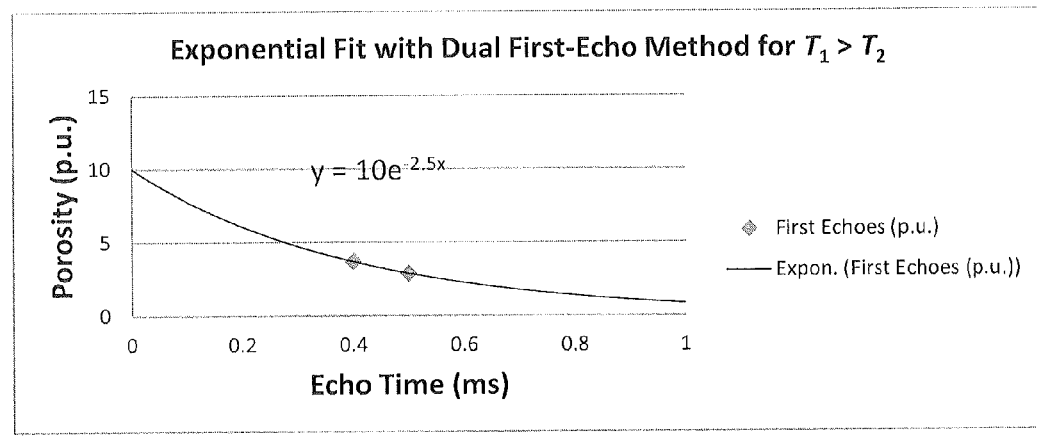
FIG. 7 depicts aspects of an exponential fit with the dual-first echo method for the case $T_1 > T_2$.

In a second simulation case, $T_1$ is greater than $T_2$. If $T_1>T_2$ then the amplitude of the first echo does not change, but the amplitude of all subsequent echoes is affected by the second-order stimulated-echo effect. As a consequence the amplitude of the subsequent echoes is larger. For the sake of simplicity, I assume that the amplitude will be 20% larger than in the $T_1=T_2$ case. FIG. 5 illustrates an exponential fit of a CPMG trainlet with an inter-echo time of 0.4 ms for the case $T_1>T_2$. The estimated porosity is 11.066 p.u. FIG. 6 illustrates an exponential fit of a CPMG trainlet with an inter-echo time of 0.5 ms for the case $T_1>T_2$. The estimated porosity is 10.813 p.u. FIG. 7 illustrates an exponential fit with the dual fist-echo method for the case $T_1>T_2$. The first echoes are recorded at the time of 0.4 ms and 0.5 ms. The estimated porosity is 10 p.u. and the estimated $T_2$ is 0.4 ms. If $T_1>T_2$ then the standard acquisition which uses a single CMPG trainlet delivers an inaccurate porosity. On the other hand, the dual first-echo method is not affected by the second-order stimulated-echo effect and as expected it delivers the correct porosity and the correct geometric mean $T_2$ value (See FIG. 7).

Figure 8:
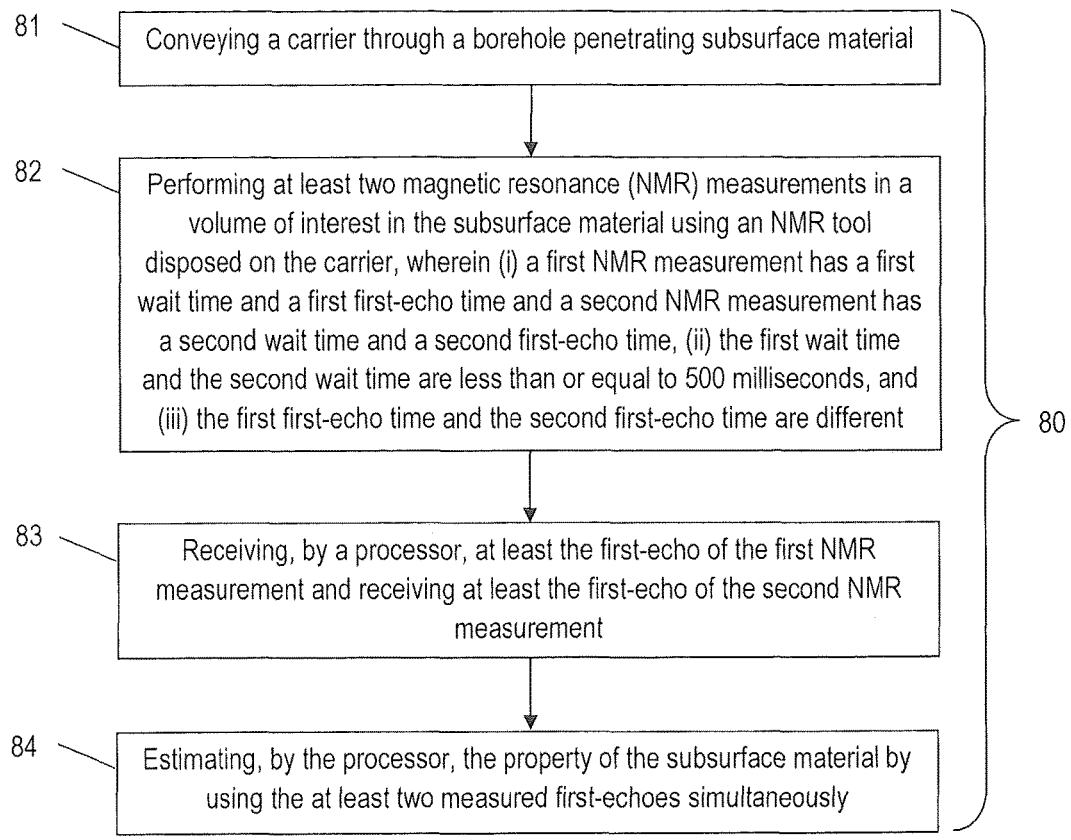
FIG. 8 is a flow chart for a method for estimating a property of a subsurface material.

FIG. 8 is a flow chart for a method 80 for estimating a property of a subsurface material. Block 81 calls for conveying a carrier through a borehole penetrating the subsurface material. Block 82 calls for performing at least two magnetic resonance (NMR) measurements in a volume of interest in the subsurface material using an NMR tool disposed on the carrier, wherein (i) a first NMR measurement has a first wait time and a first first-echo time and a second NMR measurement has a second wait time and a second first-echo time, (ii) the first wait time and the second wait time are less than or equal to 500 milliseconds, and (iii) the first first-echo time and the second first-echo time are different. In one or more embodiments, the wait time may be less than or equal to 200 ms. In one or more embodiments, the wait time may be less than or equal to 20 ms. In one or more embodiments, a difference between the first echo-time and the second echo-time is at least 0.05 milliseconds or more. Block 83 calls for receiving, by a processor, at least the first-echo of the first NMR measurement and receiving at least the first-echo of the second NMR measurement. Block 84 calls for estimating, by the processor, the property of the subsurface material by using the at least two measured first-echoes simultaneously. The term "processing" here may include inverting, exponential fit (if number of data values exceeds the number of unknowns), and exact solution (no fitting if number of data values equals the number of unknowns). In one or more embodiments, the first first-echo and the second first-echo are processed simultaneously to estimate the property. In one or more embodiments, the property is porosity or a property derived from the estimated porosity (e.g., an amount of accessible hydrocarbon reserves). In one or more embodiments, the property of the subsurface material is a $T_2$ value. In one or more embodiments, the estimated $T_2$ value is less than 3 milliseconds. In one or more embodiments, the processor is disposed in the borehole. The method 80 may include transmitting the estimated property from a first location to a second location, wherein one of the first and second location is inside the borehole while the other location is outside the borehole.

The method 80 may also include transmitting a signal comprising the property to a signal receiving device. Non-limiting embodiments of the signal receiving device include a display, a printer, and a non-transient recording medium.

The method 80 may also include constructing a property map using the estimated porosity, wherein the property map includes property values and corresponding locations of the property values in the subsurface material. The property map may be a printed map or a virtual map that can be displayed by a display or used for further computation by a processor. The method 80 may also include performing an action on the subsurface material using an action-device and the property map. In one or more embodiments, the action-device is a drilling rig configured to drill a borehole with a selected trajectory into the subsurface material. For example, the property map may show locations and corresponding amounts of hydrocarbon reserves in a formation or be an indicator for a property (e.g., clay content, hydrocarbon viscosity) of the formation. The property map can be used for a decision. Some decision examples are related to drilling, steering, completion, fluid sampling, fluid testing, hydrocarbon production, casing, and reservoir estimation. The drilling rig may then be used to drill a borehole with a selected trajectory (or geometry) to access the hydrocarbon reserves. In one embodiment, the property is the porosity of the shale and the property map is the shale porosity log (also known as the clay-bound-water volumetric). In one embodiment, the porosity log may be used for a steering action (e.g., to change the trajectory of the drill path in order to avoid a shale interval) or a stopping action (e.g., to stop drilling in case a particular shale type or clay type was intercepted). In another embodiment, the porosity log may be used for a casing decision (e.g., to decide, if casing is required or not for a drilled interval). In another embodiment, the porosity log may be used to select or change the measurement program (e.g., to select a fluid sampling point or a fluid testing point or to select the logging program for a subsequent well in the same field). In another embodiment, the porosity log may be used to calculate the hydrocarbon amount in the drilled reservoir. In another embodiment, the porosity log may be used for a production planning decision or a completion decision (e.g., the shale porosity may affect the effective porosity and the permeability and both of them may affect the interval selected for the completion). It can be appreciated that once drilling, completion or planning decisions are made, the corresponding actions may also be implemented using corresponding equipment.

The method 80 may also include: performing a third NMR measurement with a third wait time less or equal to 500 milliseconds using the NMR tool; receiving a third first-echo having a third first-echo time, wherein the third first-echo time is different from the first first-echo time and the second first-echo time; and estimating the property of the subsurface material by using the first first-echo, the second first-echo, and the third first-echo.

The method 80 may also include performing a further NMR measurement with a wait time greater than 500 milliseconds using the NMR tool; receiving at least two echoes due to the further NMR measurement using the NMR tool; and processing the first first-echo, the second first-echo, and at least two echoes from the further NMR measurement using the processor to estimate the property.

Set forth below are some embodiments of the foregoing disclosure:

Embodiment 1

A method for estimating a property of a subsurface material, the method comprising: conveying a carrier through a borehole penetrating the subsurface material; performing at least two magnetic resonance (NMR) measurements in a volume of interest in the subsurface material using an NMR tool disposed on the carrier, wherein (i) a first NMR measurement has a first wait time and a first first-echo time and a second NMR measurement has a second wait time and a second first-echo time, (ii) the first wait time and the second wait time are less than or equal to 500 milliseconds, and (iii) the first first-echo time and the second first-echo time are different; receiving, by a processor, at least the first-echo of the first NMR measurement and receiving at least the first-echo of the second NMR measurement; and estimating, by the processor, the property of the subsurface material by using the at least two measured first-echoes simultaneously.

Embodiment 2

The method according to claim 1, wherein the property of the subsurface material is a porosity.

Embodiment 3

The method according to claim 1, wherein the property of the subsurface material is a T2 value.

Embodiment 4

The method according to claim 3, wherein the estimated T2 value is less than 3 milliseconds.

Embodiment 5

The method according to claim 1, wherein estimating comprises at least one of an inversion, an exponential fit, and an exact solution of a system of equations representing the property.

Embodiment 6

The method according to claim 1, wherein the processor comprises a first processor disposed inside the borehole for receiving at least the first echo and a second processor disposed at a surface of the earth for estimating the property.

Embodiment 7

The method according to claim 1, wherein a difference between the first wait time and the second wait time is less than 200 milliseconds.

Embodiment 8

The method according to claim 1, wherein a difference between the first wait time and the second wait time is less than 20 milliseconds.

Embodiment 9

The method according to claim 1, further comprising using the estimated property to perform an action, wherein the action is one of a drilling and/or steering decision, a measurement program decision, updating a fluid model, reservoir estimation, production planning decision, and a well completion decision.

Embodiment 10

The method according to claim 1, further comprising performing an action with associated equipment using the estimated property.

Embodiment 11

The method according to claim 10, wherein the action comprises adjusting a drilling trajectory for a borehole using the estimated property and drilling the borehole in accordance with the adjusted drilling trajectory.

Embodiment 12

The method according to claim 10, wherein the action comprises: determining a fluid sampling point in the borehole using the estimated property; extracting a fluid sample at the determined fluid sampling point; and testing and/or storing the fluid sample.

Embodiment 13

The method according to claim 1, further comprising: performing a third NMR measurement with a third wait time less or equal to 500 milliseconds using the NMR tool; receiving a third first-echo having a third first-echo time, wherein the third first-echo time is different from the first first-echo time and the second first-echo time; and estimating the property of the subsurface material by using the first first-echo, the second first-echo, and the third first-echo.

Embodiment 14

The method according to claim 1, further comprising: performing a further NMR measurement with a wait time greater than 500 milliseconds using the NMR tool; receiving at least two echoes due to the further NMR measurement using the NMR tool; and processing the first first-echo, the second first-echo, and at least two echoes from the further NMR measurement using the processor to estimate the property.

Embodiment 15

The method according to claim 1, further comprising transmitting an echo and/or the estimated property from a first location to a second location, wherein one of the first and second location is inside the borehole while the other location is outside the borehole.

Embodiment 16

An apparatus for estimating a property of a subsurface material, the apparatus comprising: a carrier configured to be conveyed through a borehole penetrating the subsurface material; a nuclear magnetic resonance (NMR) tool disposed on the carrier and configured to: perform at least two magnetic resonance (NMR) measurements in a volume of interest in the subsurface material using an NMR tool disposed on the carrier, wherein (i) a first NMR measurement has a first wait time and a first first-echo time and a second NMR measurement has a second wait time and a second first-echo time, (ii) the first wait time and the second wait time are less than or equal to 500 milliseconds, and (iii) the first first-echo time and the second first-echo time are different; a processor configured to: receive at least the first-echo of the first NMR measurement and receive at least the first-echo of the second NMR measurement; and estimate the property of the subsurface material by using the at least two measured first-echoes simultaneously.

Embodiment 17

The apparatus according to claim 16, further comprising equipment for performing an action using the property, wherein the action is one of a drilling and/or steering decision, a measurement program decision, updating a fluid model, reservoir estimation, production planning decision, and a well completion decision.

Embodiment 18

The apparatus according to claim 17, wherein the equipment comprises at least one of drilling equipment configured to drill a borehole penetrating the subsurface material using the property and completion equipment configured to complete a borehole penetrating the subsurface material using the property.

Embodiment 19

The apparatus according to claim 16, wherein the NMR tool is further configured to perform a third NMR measurement with a third wait time less or equal to 500 milliseconds and receive a third first-echo having a third first-echo time, wherein the third first-echo time is different from the first first-echo time and the second first-echo time and the processor is further configured to estimate the property of the subsurface material by using the first first-echo, the second first-echo, and the third first-echo.

Embodiment 20

The apparatus according to claim 16, wherein the NMR tool is further configured to perform a further NMR measurement with a wait time greater than 500 milliseconds and receive at least two echoes due to the further NMR measurement and the processor is further configured to process the first first-echo, the second first-echo, and the at least two echoes from the further NMR measurement to estimate the property.

Embodiment 21

The apparatus according to claim 16, wherein the processor is configured to perform at least one of an inversion, an exponential fit, and an exact solution of a system of equations representing the property.

Embodiment 22

The apparatus according to claim 16, wherein a difference between the first wait time and the second wait time is less than 20 milliseconds.

Embodiment 23

The apparatus according to claim 16, further comprising Telemetry configured to transmit an echo and/or the estimated property from a first location to a second location, wherein one of the first and second location is inside the borehole while the other location is outside the borehole.

In support of the teachings herein, various analysis components may be used, including a digital and/or an analog system. For example, the NMR tool 10, the downhole electronics 11 or the computer processing system 12 may include digital and/or analog systems. The system may have components such as a processor, storage media, memory, input, output (e.g. display or printer), communications link (wired, wireless, pulsed mud, optical or other), user interfaces, software programs, signal processors (digital or analog) and other such components (such as resistors, capacitors, inductors and others) to provide for operation and analyses of the apparatus and methods disclosed herein in any of several manners well-appreciated in the art. It is considered that these teachings may be, but need not be, implemented in conjunction with a set of computer executable instructions stored on a non-transitory computer readable medium, including memory (ROMs, RAMs), optical (CD-ROMs), or magnetic (disks, hard drives), or any other type that when executed causes a computer to implement the method of the present invention. These instructions may provide for equipment operation, control, data collection and analysis and other functions deemed relevant by a system designer, owner, user or other such personnel, in addition to the functions described in this disclosure. Processed data such as a result of an implemented method may be transmitted as a signal via a processor output interface to a signal receiving device. The signal receiving device may be a computer display or a printer for presenting the result to a user. Alternatively or in addition, the signal receiving device may be a storage medium or memory for storing the result. Further, an alert maybe transmitted from the processor to a user interface if the result exceeds a threshold value. Further, the result may be transmitted to a controller or processor for executing an algorithm related to drilling or well completion that uses the result as input.

Further, various other components may be included and called upon for providing for aspects of the teachings herein. For example, a power supply (e.g., at least one of a generator, a remote supply and a battery), cooling component, heating component, magnet, electromagnet, sensor, electrode, transmitter, receiver, transceiver, antenna, controller, optical unit, electrical unit or electromechanical unit may be included in support of the various aspects discussed herein or in support of other functions beyond this disclosure.

The term "carrier" as used herein means any device, device component, combination of devices, media and/or member that may be used to convey, house, support or otherwise facilitate the use of another device, device component, combination of devices, media and/or member. Other exemplary non-limiting carriers include drill strings of the coiled tube type, of the jointed pipe type and any combination or portion thereof. Other carrier examples include casing pipes, wirelines, wireline sondes, slickline sondes, drop shots, bottom-hole-assemblies, drill string inserts, modules, internal housings and substrate portions thereof.

Elements of the embodiments have been introduced with either the articles "a" or "an." The articles are intended to mean that there are one or more of the elements. The terms "including" and "having" and the like are intended to be inclusive such that there may be additional elements other than the elements listed. The conjunction "or" when used with a list of at least two terms is intended to mean any term or combination of terms. The term "configured" relates one or more structural limitations of a device that are required for the device to perform the function or operation for which the device is configured. The term "first-echo" relates to a first (i.e., initial) echo of an echo train. The term "second-echo" relates to a second echo (i.e., immediately following the initial echo) of an echo train. The terms "first," "second" and the like not immediately followed by a hyphen are intended to distinguish different elements and do not denote a particular order.

The flow diagram depicted herein is just an example. There may be many variations to this diagram or the steps (or operations) described therein without departing from the spirit of the invention. For instance, the steps may be performed in a differing order, or steps may be added, deleted or modified. All of these variations are considered a part of the claimed invention.

While one or more embodiments have been shown and described, modifications and substitutions may be made thereto without departing from the spirit and scope of the invention. Accordingly, it is to be understood that the present invention has been described by way of illustrations and not limitation.

It will be recognized that the various components or technologies may provide certain necessary or beneficial functionality or features. Accordingly, these functions and features as may be needed in support of the appended claims and variations thereof, are recognized as being inherently included as a part of the teachings herein and a part of the invention disclosed.

While the invention has been described with reference to exemplary embodiments, it will be understood that various changes may be made and equivalents may be substituted for elements thereof without departing from the scope of the invention. In addition, many modifications will be appreciated to adapt a particular instrument, situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A method for estimating a property of a subsurface material, the method comprising:
    conveying a carrier through a borehole penetrating the subsurface material;
    performing at least two magnetic resonance (NMR) measurements in a volume of interest in the subsurface material using an NMR tool disposed on the carrier, wherein (i) a first NMR measurement has a first wait time and a first first-echo time and a second NMR measurement has a second wait time and a second first-echo time, (ii) the first wait time and the second wait time are less than or equal to 500 milliseconds, and (iii) the first first-echo time and the second first-echo time are different;
    receiving, by a processor, at least a first-echo of the first NMR measurement and receiving at least a first-echo of the second NMR measurement; and
    estimating, by the processor, the property of the subsurface material by using the at least two measured first-echoes simultaneously.

2. The method according to claim 1, wherein the property of the subsurface material is a porosity.

3. The method according to claim 1, wherein the property of the subsurface material is a $T_2$ value.

4. The method according to claim 3, wherein the estimated $T_2$ value is less than 3 milliseconds.

5. The method according to claim 1, wherein estimating comprises at least one of an inversion, an exponential fit, and an exact solution of a system of equations representing the property.

6. The method according to claim 1, wherein the processor comprises a first processor disposed inside the borehole for receiving at least the first echo and a second processor disposed at a surface of the earth for estimating the property.

7. The method according to claim 1, wherein a difference between the first wait time and the second wait time is less than 200 milliseconds.

8. The method according to claim 1, wherein a difference between the first wait time and the second wait time is less than 20 milliseconds.

9. The method according to claim 1, further comprising using the estimated property to perform an action, wherein the action is one of a drilling and/or steering decision, a measurement program decision, updating a fluid model, reservoir estimation, production planning decision, and a well completion decision.

10. The method according to claim 1, further comprising performing an action with associated equipment using the estimated property.

11. The method according to claim 10, wherein the action comprises adjusting a drilling trajectory for a borehole using the estimated property and drilling the borehole in accordance with the adjusted drilling trajectory.

12. The method according to claim 10, wherein the action comprises: determining a fluid sampling point in the borehole using the estimated property; extracting a fluid sample at the determined fluid sampling point; and testing and/or storing the fluid sample.

13. The method according to claim 1, further comprising:
    performing a third NMR measurement with a third wait time less or equal to 500 milliseconds using the NMR tool;
    receiving a first-echo of the third NMR measurement having a third first-echo time, wherein the third first-echo time is different from the first first-echo time and the second first-echo time; and estimating the property of the subsurface material by using the first-echo of the first NMR measurement, the first-echo of the second NMR measurement, and the first-echo of the third NMR measurement.

14. The method according to claim 1, further comprising:
performing a further NMR measurement with a wait time greater than 500 milliseconds using the NMR tool;
receiving at least two echoes due to the further NMR measurement using the NMR tool; and
processing the first-echo of the first NMR measurement, the first-echo of the second NMR measurement, and at least two echoes from the further NMR measurement using the processor to estimate the property.

15. The method according to claim 1, further comprising transmitting an echo and/or the estimated property from a first location to a second location, wherein one of the first and second location is inside the borehole while the other location is outside the borehole.

16. An apparatus for estimating a property of a subsurface material, the apparatus comprising:
a carrier configured to be conveyed through a borehole penetrating the subsurface material;
a nuclear magnetic resonance (NMR) tool disposed on the carrier and configured to:
perform at least two magnetic resonance (NMR) measurements in a volume of interest in the subsurface material using an NMR tool disposed on the carrier, wherein (i) a first NMR measurement has a first wait time and a first first-echo time and a second NMR measurement has a second wait time and a second first-echo time, (ii) the first wait time and the second wait time are less than or equal to 500 milliseconds, and (iii) the first first-echo time and the second first-echo time are different;
a processor configured to:
receive at least a first-echo of the first NMR measurement and receive at least a first-echo of the second NMR measurement; and
estimate the property of the subsurface material by using the at least two measured first-echoes simultaneously.

17. The apparatus according to claim 16, further comprising equipment for performing an action using the property, wherein the action is one of a drilling and/or steering decision, a measurement program decision, updating a fluid model, reservoir estimation, production planning decision, and a well completion decision.

18. The apparatus according to claim 17, wherein the equipment comprises at least one of drilling equipment configured to drill a borehole penetrating the subsurface material using the property and completion equipment configured to complete a borehole penetrating the subsurface material using the property.

19. The apparatus according to claim 16, wherein the NMR tool is further configured to perform a third NMR measurement with a third wait time less or equal to 500 milliseconds and receive a first-echo of the third NMR measurement having a third first-echo time, wherein the third first-echo time is different from the first first-echo time and the second first-echo time and the processor is further configured to estimate the property of the subsurface material by using the first-echo of the first NMR measurement, the first-echo of the second NMR measurement, and the first-echo of the third NMR measurement.

20. The apparatus according to claim 16, wherein the NMR tool is further configured to perform a further NMR measurement with a wait time greater than 500 milliseconds and receive at least two echoes due to the further NMR measurement and the processor is further configured to process the first-echo of the first NMR measurement, the first-echo of the second NMR measurement, and the at least two echoes from the further NMR measurement to estimate the property.

21. The apparatus according to claim 16, wherein the processor is configured to perform at least one of an inversion, an exponential fit, and an exact solution of a system of equations representing the property.

22. The apparatus according to claim 16, wherein a difference between the first wait time and the second wait time is less than 20 milliseconds.

23. The apparatus according to claim 16, further comprising telemetry configured to transmit an echo and/or the estimated property from a first location to a second location, wherein one of the first and second location is inside the borehole while the other location is outside the borehole.

* * * * *